US012569434B2

(12) United States Patent
Dendukuri et al.

(10) Patent No.: US 12,569,434 B2
(45) Date of Patent: Mar. 10, 2026

(54) FORMULATIONS OF NEBIVOLOL

(71) Applicant: EXTROVIS AG, Baar (CH)

(72) Inventors: Vinayak Dinesh Dendukuri, Hyderabad (IN); Rajasekhara Reddy Singampalli, Hyderabad (IN)

(73) Assignee: EXTROVIS AG, Baar (CH)

( * ) Notice: Subject to any disclaimer, the term of this patent is extended or adjusted under 35 U.S.C. 154(b) by 0 days.

(21) Appl. No.: 18/450,882

(22) Filed: Aug. 16, 2023

(65) Prior Publication Data

US 2023/0390194 A1 Dec. 7, 2023

Related U.S. Application Data

(63) Continuation of application No. 17/370,205, filed on Aug. 8, 2021.

(30) Foreign Application Priority Data

Jul. 8, 2020 (IN) ............................ 202041028951

(51) Int. Cl.
*A61K 9/00* (2006.01)
*A61K 31/353* (2006.01)

(52) U.S. Cl.
CPC .......... *A61K 9/0095* (2013.01); *A61K 9/0053* (2013.01); *A61K 31/353* (2013.01)

(58) Field of Classification Search
CPC ... A61K 9/0095; A61K 9/0053; A61K 31/353
See application file for complete search history.

(56) References Cited

U.S. PATENT DOCUMENTS 4,654,362 A 3/1987 Van Lommen et al.
5,759,580 A * 6/1998 Jans .................... A61K 31/353 424/494
6,545,040 B1 4/2003 Xhonneux et al.
8,633,241 B2 1/2014 Attanti et al.
2002/0032149 A1* 3/2002 Kensey ............. A61B 5/02028 514/1
2003/0099694 A1* 5/2003 Cevc ....................... A61P 25/08 424/449
2005/0272810 A1 12/2005 Davis et al.
2006/0182796 A1* 8/2006 Wu ...................... A61K 9/5078 424/464
2008/0242687 A1 10/2008 Gant et al.
2008/0300316 A1* 12/2008 Gant ....................... A61P 25/06 564/305
2009/0215844 A1* 8/2009 Davis ..................... A61K 45/06 514/412
2012/0093922 A1* 4/2012 Manku ...................... A61P 9/12 424/490
2015/0231261 A1* 8/2015 Akbarieh ............ A61K 9/2059 514/456
2020/0197468 A1* 6/2020 Housey .................... A61K 8/19

FOREIGN PATENT DOCUMENTS

WO 2006084684 A1 8/2006

* cited by examiner

*Primary Examiner* — Robert A Wax
*Assistant Examiner* — Olga V. Tcherkasskaya
(74) *Attorney, Agent, or Firm* — MEDLER FERRO WOODHOUSE & MILLS PLLC

(57) ABSTRACT

The present disclosure provides a formulation comprising: 0.05 to 10% (w/w) of Nebivolol or a pharmaceutically acceptable salt thereof; 0.4 to 10% (w/w) of a solubilizer; and 5 to 90% (w/w) of a sweetener, wherein the formulation has pH in the range of 3 to 7. The present disclosure provides a reconstituted formulation comprising the formulation with a liquid vehicle. The present disclosure also provides process of preparing the formulations and methods thereof.

7 Claims, No Drawings

FORMULATIONS OF NEBIVOLOL

FIELD OF INVENTION

The present disclosure relates to formulations of Nebivolol or pharmaceutically acceptable salts thereof. The present disclosure in particular relates to oral formulations of Nebivolol or pharmaceutically acceptable salts thereof. The present disclosure further relates to process of preparing the formulations and implementations of the formulations thereof.

BACKGROUND OF THE INVENTION

Nebivolol is chemically known as (1RS,1'RS)-1,1'-[(2RS, 2'SR)-bis(6-fluoro-3,4-dihydro-2H-1-benzopyran-2-yl)]-2, 2'-iminodiethanol hydrochloride. Nebivolol is a racemate composed of d-Nebivolol and 1-Nebivolol with the stereochemical designations of [SRRR]-nebivolol and [RSSS]-nebivolol, respectively. Nebivolol's molecular formula is ($C_{22}H_{25}F_2NO_4$·HCl) with the following structural formula:

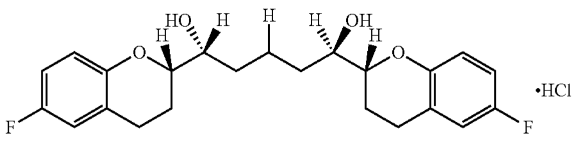

SRRR- or d-nebivolol hydrochloride

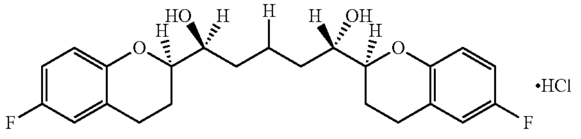

RSSS- or l-nebivolol hydrochloride

Nebivolol is a highly selective beta-1 blocker and is mainly used for the treatment and prevention of coronary vascular disorders. Nebivolol is indicated for the treatment of hypertension, to lower blood pressure and may be used alone or in combination with other antihypertensive agents. It is taken once or twice a day as per the requirement of the patient.

In extensive metabolizers (most of the population) and at doses less than or equal to 10 mg, Nebivolol is preferentially β1 selective. In poor metabolizers and at higher doses, Nebivolol inhibits both β1- and β2-adrenergic receptors. Nebivolol lacks intrinsic sympathomimetic and membrane stabilizing activity at therapeutically relevant concentrations. At clinically relevant doses, Nebivolol does not demonstrate al-adrenergic receptor blockade activity. Various metabolites, including glucuronides, contribute to β-blocking activity.

A major problem in the development of pharmaceutical compositions comprising Nebivolol is its poor solubility and, concomitantly, the poor release and low bioavailability of the active ingredient. Pharmaceutical compositions containing Nebivolol are currently marketed in the US and various other countries under the brand name "Bystolic®" in the form of tablets.

It is generally known that certain segments of the population have difficulty in ingesting and swallowing solid oral dosage forms such as tablets and capsules. As many as a quarter of the total population has this difficulty. Further, solid dosage forms are not recommended for children or elderly due to increased risk in choking. Often, this leads to non-compliance with the recommended medical therapy with the solid dosage forms, thereby resulting in rending the therapy ineffective. Further Nebivolol is bitter in taste. There has been a long-left need for taste masked oral liquid formulation of Nebivolol for treating hypertension. This approach leads to good results for geriatric patients who cannot swallow tablets or capsules especially when they are certain dimensional limits.

Nebivolol and its tablet formulation is first disclosed in U.S. Pat. No. 4,654,362A. U.S. Pat. No. 6,545,040 discloses method of lowering the blood pressure using Nebivolol.

U.S. Pat. No. 8,633,241B2 disclose solid oral dosage form of Nebivolol hydrochloride without the use of wetting agent, and optionally using binder and/or disintegrant.

WO 2006/084684A1 disclose pharmaceutical compositions comprising Nebivolol and a hydrophilic polymer.

The oral liquid formulations are advantageous over conventional solid dosage administration of Nebivolol due to ease of administration, an increased patient compliance to medication and accessibility to additional patient populations such as to children and the elderly.

Hence there is a dire need in the state of art to provide stable Nebivolol oral liquid formulations in the form of fully liquid as well as powder formulations for reconstitution for oral liquid administration.

SUMMARY OF THE INVENTION

In first aspect of the present disclosure, there is provided a formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7.

In second aspect of the present disclosure, there is provided a reconstituted formulation comprising the formulation comprising: a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; and i) 0.01 to 2% (w/w) of a coloring agent, wherein the formulation has pH in the range of 3 to 7.

In third aspect of the present disclosure, there is provided a reconstituted formulation comprising the formulation comprising: a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; i) 0.01 to 2% (w/w) of a coloring agent; and j) 65 to 95% (w/w) of a liquid vehicle, wherein the formulation has pH in the range of 3 to 7.

In fourth aspect of the present disclosure, there is provided a formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, reconstituted with a liquid vehicle, wherein the reconstituted formulation is stable for a time period in the range of 30 days to one year; and the formulation has pH in the range of 3 to 7.

In fifth aspect of the present disclosure, there is provided a process of preparing the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7, the process comprising: i) adding nebivolol or a pharmaceutically acceptable salt thereof with a solubilizer to obtain a first mixture; and ii) blending the first mixture with a sweetener to obtain the formulation.

In sixth aspect of the present disclosure, there is provided a pharmaceutical composition comprising the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, with other pharmaceutically active compound, wherein the formulation has pH in the range of 3 to 7.

In seventh aspect of the present disclosure, there is provided use of the formulation comprising: a) 0.05 to 10% (w/w) of Nebivolol or a pharmaceutically acceptable salt thereof, b) 0.4 to 10% (w/w) of a solubilizer; and c) 5 to 90% (w/w) of a sweetener, wherein the formulation has pH in the range of 3 to 7, as a beta-blocker and/or for abnormal blood pressure.

In eighth aspect of the present disclosure, there is provided a kit comprising: a) the formulation comprising: i) 0.05 to 10% (w/w) of Nebivolol or a pharmaceutically acceptable salt thereof; ii) 0.4 to 10% (w/w) of a solubilizer; and iii) 5 to 90% (w/w) of a sweetener; and b) a liquid vehicle, wherein the formulation has pH in the range of 3 to 7.

In ninth aspect of the present disclosure, there is provided an oral pharmaceutical dosage form comprising a dosing unit comprising the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7; and Nebivolol or a pharmaceutically acceptable salt thereof is in a final concentration equivalent to between 0.1 mg nebivolol HCl per ml liquid vehicle and 50 mg nebivolol HCl per ml liquid vehicle.

In tenth aspect of the present disclosure, there is provided a method of administration in an individual in need thereof, the method comprising: administering a first amount of the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the first amount of the formulation comprises Nebivolol or a pharmaceutically acceptable salt thereof in a final concentration equivalent to between 0.1 mg nebivolol HCl per ml liquid vehicle and 50 mg nebivolol HCl per ml liquid vehicle.

In eleventh aspect of the present disclosure, there is provided a method of treating or preventing a condition, disorder, or disease mediated by beta-blocking, the method comprising: administering an effective amount of the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7 or the pharmaceutical composition, to a subject in need thereof.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "at least one" is used to mean one or more and thus includes individual components as well as mixtures/combinations.

Nebivolol as used herein may be present in crystallize or amorphous form. The particle size of Nebivolol used as per the invention may range from 1 to 100 microns, preferably, d90 less than 20 microns. The major impurities of Nebivolol are Desfluoro Nebivolol and 4-Benzylated Nebivolol. The oral liquid formulations of the present invention are stable and the presence these impurities are less than 1%.

The term "pharmaceutically acceptable salts thereof" as used herein refers to compounds or compositions that are physiologically tolerable and do not typically produce allergic or similar untoward reaction, including but not limited to gastric upset or dizziness when administered to subjects. Pharmaceutically acceptable salts forming part of this invention include addition salts derived from acids, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propane-tricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. In the present disclosure, pharmaceutically acceptable salts thereof includes but not limited to salts of Nebivolol selected from hydrochloric acid, hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, methanesulfonic acid, ethanesulfonic acid, benzenesulfonic acid, 4-methylbenzenesulfonic acid, 2-hydroxybenzoic acid, or 4-amino-2-hydroxybenzoic acid. In the present disclosure, the amount of Nebivolol included in the formulation, as calculated on the basis of the HCl salt, is from about 0.1 mg/mL to 50 mg/mL, may be 1 mg/ml, 0.8 mg/ml, 40 mg/ml, 30 mg/ml, 20 mg/ml, 10 mg/ml, and the like.

The term "solubilizer" as used herein refers to solubility enhancer Solubilizer or solubility enhancer and may be used interchangeably. Suitable solubilizer or solubility enhancers include water-soluble organic solvents such as polyethylene glycol 300, polyethylene glycol 400, ethanol, propylene glycol, glycerin; anionic surfactant such as sodium lauryl sulfate, docusate sodium and the like; non-ionic surfactants such as CREMOPHOR EL, CREMOPHOR RH 40, CREMOPHOR RH 60, d-alpha-tocopherol polyethylene glycol 1000 succinate, polysorbate 20, polysorbate 80, sorbitan monooleate, poloxamer, poloxamer 188, poloxamer 407, LABRAFIL M-1944CS, LABRAFIL M-2125CS, LABRASOL, GELLUCIRE 44/14, SOFTIGEN 767, and mono- and di-fatty acid esters such as polyethylene glycol PEG 300, PEG 400, PEG 1750, or PEG 4000, cyclodextrin, CAPTISOL and the like.

The term "sweetener" as used herein refers to a substance providing sweet taste and has taste similar to a sugar to make the product more palatable. This includes natural and synthetic sugars, natural and artificial sweeteners, natural extracts, and any material that initiates a sweet sensation in a subject. In some implementation, a solid/powder sweetener is used in the oral liquid formulation and a liquid sweetener is used in the oral liquid formulation described herein. The amount of sweetener may vary depending on the sweetener used and may range from 1 mg to 500 mg/ml, 1 mg to 400 mg/ml, or 10 mg to 350 mg/ml.

Sweeteners or sugars illustratively include glucose, fructose, sucrose, xylitol, tagatose, sucralose, maltitol, isomaltulose, isomaltulose, lactitol, sorbitol, erythritol, trehalose, maltodextrin, polydextrose, and the like. Other sweeteners illustratively include glycerin, inulin, erythritol, acesulfame, and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrosylates, maltitol syrup, high fructose corn syrup, and as branded proprietary blend products. Sweeteners can be used singly or combinations of two or more. Suitable concentrations of different sweeteners can be selected based on published information, manufacturers' data sheets, and by routine testing.

The term "flavouring agent" as used herein refers to a substance that provides enhanced the taste or aroma to the formulation. Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. Also useful, particularly where the composition is intended primarily for pediatric use is tutti-frutti or bubble gum flavor, a compounded flavoring agent based on fruit flavors. Presently, preferred flavoring agents include bubble gum, strawberry, cherry, grape, orange, peppermint, and vanilla. In some implementation, the resultant liquid form from the Nebivolol hydrochloride powder or granules described herein comprises a grape (specifically, white grape) flavoring agent. Flavoring agents may be used singly or in combinations of two or more.

The term "preservative" as used herein refers to a compound that provides anti-microbial effect to the formulation, preservative is used in an amount sufficient to provide antimicrobial effectiveness to the Nebivolol oral liquid formulation described herein. Preservatives include anti-microbials, anti-oxidants, and agents that enhance sterility. Suitable preservatives include ascorbic acid, ascorbyl palmitate, benzyl alcohol, butylated hydroxyanisole (BHA), butylated hydroxytoluene (BHT), erythorbic acid, fumaric acid, malic acid, propyl gallate, sodium ascorbate, sodium benzoate, sodium bisulfate, sodium metabisulfite, sodium sulfite, methyl paraben, propylparaben, benzoic acid, potassium sorbate, and vanillin. In some implementation, the Nebivolol hydrochloride powder described herein, when compounded into a liquid form, or in multiple dosage form comprises a preservative. The amount of preservative used may range from about 0.5 to 20 mg/ml.

The term "binder" or "thickener" as used herein refers to substance that impart viscosity or weight to the formulation. Exemplary binders/thickeners include dextrin, cellulose derivatives (hydroxypropyl cellulose, ethylcellulose, hydroxyethyl cellulose, methylcellulose, polyvinylpyrrolidone (povidone or PVP K-90), hypromellose, and the like) starches, gelatin, pectin, polyethylene oxide, and certain gums (xanthan gum, locust bean gum, etc).

The term "buffer" or "buffering agent" as used herein refers to a substance or compound used to maintain the pH of the formulation. Buffering agents maintain the pH when Nebivolol hydrochloride powder is compounded into a liquid form or the liquid solution or suspension. Examples of suitable buffering agents include, but are not limited to, sodium bicarbonate, potassium bicarbonate, magnesium hydroxide, magnesium lactate, magnesium gluconate, aluminum hydroxide, aluminum hydroxide/sodium bicarbonate precipitate, a mixture of an amino acid and a buffer, a mixture of aluminum glycinate and a buffer, a mixture of acid salt and an amino acid and a buffer, and a mixture of an alkali salt of an amino acid and a buffer. Additional buffering agents include citric acid, sodium citrate, sodium tartrate, sodium acetate, sodium carbonate, sodium polyphosphate, potassium polyphosphate, sodium pyrophosphate, potassium pyrophosphate, disodium hydrogenphosphate, trisodium phosphate or sodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when Nebivolol hydrochloride powder is compounded into a liquid. In some implementation, the Nebivolol hydrochloride powder described herein, when compounded into a liquid form, comprises a buffering agent. The amount of buffer used may range from 0.1 mg to 100 mg/ml, preferably 1 mg to 50 mg, 2 mg to 50 mg/ml.

The term "coloring agent" as used herein refers to a substance added to identity and/or for aesthetic purposes. Suitable coloring agents approved by the U.S. Food and Drug Administration (FDA) include FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide and mixtures thereof. The resultant liquid form from the Nebivolol hydrochloride powder/granules described herein displays an amber-colored appearance for identity and aesthetic purposes associated with a white grape flavor.

The term "glidant" as used herein refers to substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc, and the like.

The term "liquid vehicle" or "diluent" as used herein refers to a solvent or liquid present in the formulation, and the formulation is in liquid form. Liquid vehicles/diluent for compounding the Nebivolol powder formulations into an oral solution are also described herein. Exemplary liquid vehicles include water, ethyl alcohol, glycerin, syrup (sugar or other sweetener based, e.g., ORA-SWEET® SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof.

Certain liquid vehicles, e.g., oil and water, can be combined together to form emulsions. In some implementation, water is used for as a vehicle for a Nebivolol oral liquid formulation. In other implementation, a syrup is used for as a vehicle for a Nebivolol oral liquid formulation. In yet other implementation, a juice is used for as a vehicle for a Nebivolol oral liquid formulation. The liquid is selected for a particular oral liquid formulation (solution, suspension, etc.) as well as other qualities such as clarity, toxicity, viscosity, compatibility with excipients, chemical inertness, palatability, odor, color and economy. The liquid vehicle optionally comprising one or more excipients selected from flavouring agent, preservative, binder, buffer, coloring agent, glidant, or combination thereof.

The term "pharmaceutically active compound" used herein refers to other compounds that are pharmaceutically active and that can be used in combination with the formulation of the present disclosure. The other pharmaceutically active compounds include but not limited to diuretics such as loop, thiazide, potassium-sparing, and the like, beta blockers such as metoprolol, propanolol, pronethalol, and the like, alpha blockers such as phentolamine, phenoxybenzamine, tamsulosin, prazosin, and the like, mixed alpha and beta blockers such as bucindolol, carvedilol, labetalol, calcium channel blockers such as dihydropyridines such as nifedipine, amlodipine, etc., dilitazem, verapamil and the like, angiotensin II receptor antagonists such as saralasin, losartan, eprosartin, irbesartan, valsartan, and the like), other ACE Angiotensin-converting enzyme (ACE) inhibitors such as captopril, lisinopril, quinapril, ramipril, enalapril, zofenopril, and the like), aldosterone antagonists such as eplerenone, spironolactone and the like, vasodilators such as hydralazine and the like, or alpha-2 agonists such as clonidine, moxonidine, guanabenz and the like.

The compounded solution of the invention is prepared by mixing a powder form of Nebivolol hydrochloride with a liquid solution, also referred to as a diluent. The liquid solution or diluent of the invention imparts improved properties on the compounded solution. An optimal liquid solution can impart on the compounded solution enhanced stability at room temperature without interfering with the activity of the Nebivolol hydrochloride.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight percentage range of 0.05 to 10% (w/w) should be interpreted to include not only the explicitly recited limits of 0.05% (w/w) to 10% (w/w) but also to include sub-ranges, such as 0.06% to 9% (w/w), 0.1% to 7% (w/w) and so forth, as well as individual amounts, including fractional amounts, within the specified ranges, such as 0.062%, 0.09%, 0.88%, 0.9%, and 1.39% for example.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific implementation described herein, which are intended for the purposes of exemplification only. Functionally-equivalent products, compositions, and methods are clearly within the scope of the disclosure, as described herein.

As discussed in the background, pediatric and geriatric populations encounter difficulty being administered solid oral dosage forms such as capsules. And also the solid dosage forms are not recommended for children or elderly due to increased risk of choking. This may lead to non-compliance with the recommended pharmacotherapy with the solid oral dosage forms and likely results in rendering the therapy ineffective. Additionally, certain solid oral dosage forms of medications cannot be administered simply by crushing (for example patients requiring various types of feeding tubes), because of the coating or drug delivery mechanism by which the drug is released. To overcome disadvantages associated with the use of the tablet form, compounding pharmacist pulverizes and crush the tablet(s) into a powder via mortar and pestle and reconstitute the powder in some liquid form. However, forming an oral liquid in this fashion has significant drawbacks including large variability in the actual dosage, incomplete solubilizing of the tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or another crushing agent. Thus, the present invention overcomes aforementioned drawbacks of the solid oral dosage form of Nebivolol hydrochloride by providing a formulation comprising Nebivolol with a solubilizer and a sweetener. The present invention also provides a formulation with a liquid vehicle.

According to an implementation of the present disclosure, there is provided a formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7. In an alternate implementation, there is provided a formulation comprising: a) 0.05 to 5% (w/w) of Nebivolol or a pharmaceutically acceptable salt thereof; b) 0.4 to 9% (w/w) of a solubilizer; and c) 5 to 89% (w/w) of a sweetener. In other implementation, there is provided a formulation comprising: a) 0.05 to 4% (w/w) of Nebivolol or a pharmaceutically acceptable salt thereof; b) 0.5 to 9% (w/w) of a solubilizer; and c) 6 to 89% (w/w) of a sweetener.

According to an implementation of the present disclosure, there is provided a formulation as disclosed herein, wherein Nebivolol or a pharmaceutically acceptable salt thereof is Nebivolol hydrochloride.

According to an implementation of the present disclosure, there is provided a formulation comprising: a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; and i) 0.01 to 2% (w/w) of a coloring agent, wherein the formulation has pH in the range of 3 to 7.

According to an implementation of the present disclosure, there is provided a formulation comprising: a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; i) 0.01 to 2% (w/w) of a coloring agent; and j) 65 to 95% (w/w) of a liquid vehicle, wherein the formulation has pH in the range of 3 to 7.

According to an implementation of the present disclosure, there is provided a formulation as disclosed herein, wherein the solubilizer is selected from cyclodextrin, propylene glycol, polyethylene glycol, polysorbate 20, polysorbate 80, sorbitan monooleate, poloxamer, sodium lauryl sulfate, CAPTISOL, LABRASOL, or combinations thereof, and the sweetener is selected from natural and synthetic sugars, natural and artificial sweeteners, natural extracts. In another implementation of the present disclosure, there is provided a formulation as disclosed herein, wherein the solubilizer is selected from sodium lauryl sulfate, propylene glycol, polyethylene glycol, poloxamer, or combinations thereof.

According to an implementation of the present disclosure, there is provided a formulation as disclosed herein, wherein the sweetener is selected from glucose, fructose, sucrose, xylitol, tagatose, sucralose, maltitol, isomaltulose, isomaltulose, lactitol, sorbitol, eiythritol, trehalose, maltodextrin, polydextrose, glycerin, inulin, erythritol, acesulfame, saccharin sodium, saccharin calcium, neohesperidin dihydrochalcone, stevioside, thaumatin, or combinations thereof. In another implementation of the present disclosure, there is provided a formulation as disclosed herein, wherein the sweetener is selected from sorbitol, xylitol, sucralose, maltitol, saccharin sodium, or combinations thereof.

According to an implementation of the present disclosure, there is provided a formulation as disclosed herein, wherein the formulation comprises one or more liquid vehicle.

According to an implementation of the present disclosure, there is provided a formulation as disclosed herein, wherein the formulation comprises one or more liquid vehicle selected from water, ethyl alcohol, glycerin, syrup, beverage, juices, or combinations thereof in the weight range of 65 to 95% (w/w) of the formulation. In an alternate implementation, the formulation comprises a liquid vehicle in the weight range of 65 to 94% (w/w) of the formulation. In another alternate implementation, the formulation comprises a liquid vehicle in the weight range of 65 to 93% (w/w) of the formulation. In one another alternate implementation, the formulation comprises a liquid vehicle in the weight range of 67 to 90% (w/w) of the formulation.

According to an implementation of the present disclosure, there is provided a formulation as disclosed herein, wherein the formulation comprises water or juice as liquid vehicle. In an alternate implementation, there is provided a formulation as disclosed herein, wherein the formulation comprises water as liquid vehicle.

According to an implementation of the present disclosure, there is provided a formulation as disclosed herein, wherein the formulation comprises an excipient selected from a flavouring agent, a preservative, a binder, a buffer, a glidant, a coloring agent, or combinations thereof.

According to an implementation of the present disclosure, there is provided a formulation as disclosed herein, wherein the flavouring agent is in the weight range of 0.05 to 20% (w/w) of the formulation; the preservative is in the weight range of 0.05 to 20% (w/w) of the formulation; the binder is in the weight range of 0.5 to 20% (w/w) of the formulation; the buffer is in the weight range of 0.025 to 15% (w/w) of the formulation; the glidant is in the weight range of 0.1 to 3.0% (w/w) of the formulation; and the coloring agent is in the weight range of 0.01 to 2% (w/w) of the formulation. In an alternate implementation, there is provided a formulation as disclosed herein, wherein the flavouring agent is in the weight range of 0.05 to 15% (w/w) of the formulation; the preservative is in the weight range of 0.05 to 15% (w/w) of the formulation; the binder is in the weight range of 0.5 to 15% (w/w) of the formulation; the buffer is in the weight range of 0.025 to 10% (w/w) of the formulation; the glidant is in the weight range of 0.1 to 2.0% (w/w) of the formulation; and the coloring agent is in the weight range of 0.01 to 1% (w/w) of the formulation.

In an alternate implementation, there is provided a formulation as disclosed herein, wherein the flavouring agent is in the weight range of 0.05 to 10% (w/w) of the formulation; the preservative is in the weight range of 0.05 to 10% (w/w) of the formulation; the binder is in the weight range of 0.5 to 10% (w/w) of the formulation; the buffer is in the weight range of 0.025 to 5% (w/w) of the formulation; the glidant is in the weight range of 0.1 to 1.0% (w/w) of the formulation; and the coloring agent is in the weight range of 0.01 to 0.5% (w/w) of the formulation.

According to an implementation of the present disclosure, there is provided a formulation as disclosed herein, wherein the flavouring agent is selected from strawberry, cherry, grape, orange, peppermint, vanilla, bubble gum, or combinations thereof. In an alternate implementation, there is provided a formulation as disclosed herein, wherein the flavouring agent is selected from strawberry, grape, orange, or combinations thereof.

According to an implementation of the present disclosure, there is provided a formulation as disclosed herein, wherein the preservative is selected from ascorbic acid, benzyl alcohol butylated hydroxyanisole (BHA), butylated hydroxytoluene (BUT), sodium benzoate, sodium bisulfate, sodium metabisulfite, sodium sulfite, methyl paraben, propylparaben, benzoic acid, potassium sorbate, or combinations thereof. In an alternate implementation, there is provided a formulation as disclosed herein, wherein the preservative is selected from sodium benzoate, methyl paraben, propylparaben, or combinations thereof.

According to an implementation of the present disclosure, there is provided a formulation as disclosed herein, wherein the binder is selected from polyvinylpyrrolidone, ethylcellulose, hydroxyethyl cellulose, hydroxypropyl cellulose, methylcellulose, hypromellose, gelatine, starch, trehalose, gums, or combinations thereof. In an alternate implementation, there is provided a formulation as disclosed herein, wherein the binder is polyvinylpyrrolidone.

According to an implementation of the present disclosure, there is provided a formulation as disclosed herein, wherein the buffer is selected from citric acid, sodium bicarbonate, potassium bicarbonate, magnesium hydroxide, magnes citric acid, sodium citrate, sodium tartrate, sodium acetate, sodium carbonate, sodium polyphosphate, potassium polyphosphate, sodium pyrophosphate, potassium pyrophosphate, disodium hydrogenphosphate, trisodium phosphate, tripotassium phosphate, sodium acetate, or combinations thereof. In an alternate implementation, there is provided a formulation as disclosed herein, wherein the buffer is selected from citric acid, sodium polyphosphate, sodium pyrophosphate, trisodium phosphate, or combinations thereof.

According to an implementation of the present disclosure, there is provided a formulation as disclosed herein, wherein the glidant is selected from calcium phosphate tribasic, calcium silicate, cellulose, colloidal silicon dioxide, magnesium silicate, magnesium trisilicate, silicon dioxide, starch, talc, or combinations thereof; and the coloring agent is selected from FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide, or combinations thereof. In an alternate implementation, there is provided a formulation as disclosed herein, wherein the glidant is silicon dioxide.

According to an implementation of the present disclosure, there is provided a formulation as disclosed herein, wherein the formulation comprises 0.1 to 50 mg/ml of Nebivolol or a pharmaceutically acceptable salt thereof; 0.1 to 300 mg/ml of a solubilizer; and 5 to 400 mg/ml of a sweetener.

According to an implementation of the present disclosure, there is provided a formulation as disclosed herein, wherein the formulation comprises 0.1 to 50 ml of the liquid vehicle. In an alternate implementation, there is provided a formulation as disclosed herein, wherein the formulation comprises 0.1 to 45 ml of the liquid vehicle. In another implementation, there is provided a formulation as disclosed herein, wherein the formulation comprises 0.1 to 40 ml of the liquid vehicle.

According to an implementation of the present disclosure, there is provided a formulation as disclosed herein, wherein the formulation comprises 0.5 to 100 mg/ml of a flavouring agent; 0.5 to 50 mg/ml of a preservative; 0.5 to 20 mg/ml of a binder, 0.1 to 100 mg/ml of a buffer; 0.025 to 10 mg/ml of a glidant; and 0.01 to 20 mg/ml of a coloring agent.

According to an implementation of the present disclosure, there is provided a formulation as disclosed herein, wherein the formulation is a stable oral formulation for administration as a liquid.

According to an implementation of the present disclosure, there is provided a formulation comprising: a) 0.1 to 50 mg/ml Nebivolol or a pharmaceutically acceptable salt thereof; b) 0.1 to 300 mg/ml of a solubilizer; c) 0.5 to 400 mg/ml sweetener; d) 0.5 to 100 mg/ml of a flavouring agent; e) 0.5 to 50 mg/ml of a preservative; f) 0.5 to 20 mg/ml of a binder, g) 0.1 to 100 mg/ml of a buffer; h) 0.025 to 10 mg/ml of a glidant; and i) 0.01 to 20 mg/ml of a coloring agent, wherein the formulation has pH in the range of 3 to 7.

According to an implementation of the present disclosure, there is provided a formulation comprising: a) 0.1 to 50 mg/ml Nebivolol or a pharmaceutically acceptable salt thereof; b) 0.1 to 300 mg/ml of a solubilizer; c) 0.5 to 400 mg/ml sweetener; d) 0.5 to 100 mg/ml of a flavouring agent; e) 0.5 to 50 mg/ml of a preservative; f) 0.5 to 20 mg/ml of a binder, g) 0.1 to 100 mg/ml of a buffer; h) 0.025 to 10 mg/ml of a glidant; i) 0.01 to 20 mg/ml of a coloring agent; and j) 0.1 to 50 ml of the liquid vehicle, wherein the formulation has pH in the range of 3 to 7.

According to an implementation of the present disclosure, there is provided a formulation comprising: a) 0.1 to 50 mg/ml Nebivolol or a pharmaceutically acceptable salt thereof; b) 0.1 to 300 mg/ml of a solubilizer; c) 0.5 to 400 mg/ml sweetener; and d) 0.5 to 20 mg/ml of a flavouring agent, wherein the formulation has pH in the range of 3 to 7.

According to an implementation of the present disclosure, there is provided a formulation comprising: a) 0.5 to 10 mg/ml Nebivolol or a pharmaceutically acceptable salt thereof; b) 1 to 20 mg/ml of a solubilizer; c) 70 to 200 mg/ml sweetener; d) 1 to 5 mg/ml of a flavouring agent, and e) 7 to 12 mg/ml of a binder wherein the formulation has pH in the range of 3 to 7.

According to an implementation of the present disclosure, there is provided a formulation comprising: a) 0.5 to 10 mg/ml Nebivolol or a pharmaceutically acceptable salt thereof; b) 1 to 20 mg/ml of a solubilizer; c) 70 to 200 mg/ml sweetener; d) 1 to 5 mg/ml of a flavouring agent, and e) 7 to 12 mg/ml of a binder with the liquid vehicle in an amount ranging from Qs (quantity sufficient) to 1 ml, wherein the formulation has pH in the range of 3 to 7.

According to an implementation of the present disclosure, there is provided a formulation comprising: a) 0.5 to 10 mg/ml Nebivolol or a pharmaceutically acceptable salt thereof; b) 1 to 20 mg/ml of a solubilizer; c) 70 to 200 mg/ml sweetener; d) 0.5 to 1 mg/ml of a flavouring agent, and e) 0.5 to 1 mg/ml of a preservative, with the liquid vehicle in an amount ranging from Qs to 1 ml, wherein the formulation has pH in the range of 3 to 7.

According to an implementation of the present disclosure, there is provided a formulation comprising: a) 0.5 to 10 mg/ml Nebivolol or a pharmaceutically acceptable salt thereof; b) 5 to 20 mg/ml of a solubilizer; c) 70 to 200 mg/ml sweetener; d) 1 to 3 mg/ml of a flavouring agent; e) 0.5 to 2 mg/ml of a preservative; f) 0.1 to 1 mg/ml of a buffer; and j) Qs to 1 ml of the liquid vehicle, wherein the formulation has pH in the range of 3 to 7.

According to an implementation of the present disclosure, there is provided a formulation comprising: a) 0.1 to 50 mg/ml Nebivolol or a pharmaceutically acceptable salt thereof; b) 0.1 to 300 mg/ml of a solubilizer; c) 0.5 to 400 mg/ml sweetener; d) 0.5 to 100 mg/ml of a flavouring agent, e) 0.5 to 20 mg/ml of a binder; and the liquid vehicle, wherein the formulation has pH in the range of 3 to 7, and the formulation is homogenous and stable for at least 30 days at ambient and refrigerated temperature and has 95% w/w or greater of the initial Nebivolol amount and 5% w/w or less total impurities or related substances at the end of the given storage period.

According to an implementation of the present disclosure, there is provided a formulation comprising: a) 0.1 to 50 mg/ml Nebivolol or a pharmaceutically acceptable salt thereof; b) 0.1 to 300 mg/ml of a solubilizer; c) 0.5 to 400 mg/ml sweetener; d) 0.5 to 100 mg/ml of a flavouring agent, e) 0.5 to 20 mg/ml of a binder; and the liquid vehicle, wherein the formulation has pH in the range of 3 to 7 and is stable at about 25±5° C. for a time period of one month to 12 months.

According to an implementation of the present disclosure, there is provided a stable water soluble granule formulation comprising: a) 0.1 to 50 mg/ml Nebivolol or a pharmaceutically acceptable salt thereof; b) 0.1 to 300 mg/ml of a solubilizer; c) 0.5 to 400 mg/md sweetener; d) 0.5 to 100 mg/ml of a flavouring agent, and e) 0.5 to 20 mg/ml of a binder, wherein the formulation has pH in the range of 3 to 7; and said granules are administered as oral liquid by dissolving in the liquid vehicle.

According to an implementation of the present disclosure, there is provided a reconstituted formulation comprising the formulation comprising a) 0.05 to 10% (w/w) of Nebivolol or a pharmaceutically acceptable salt thereof; b) 0.4 to 10% (w/w) of a solubilizer; and c) 5 to 90% (w/w) of a sweetener with a liquid vehicle, wherein the reconstituted formulation is stable for a time period in the range of 30 days to one year, and the formulation has pH in the range of 3 to 7.

According to an implementation of the present disclosure, there is provided a formulation comprising: a) 0.1 to 2% (w/w) of Nebivolol or a pharmaceutically acceptable salt thereof; b) 5 to 10% (w/w) of a solubilizer; c) 70 to 90% (w/w) of a sweetener; d) 0.1 to 1% (w/w) of a flavouring agent; and e) 0.5 to 1% (w/w) of a preservative, wherein the formulation has pH in the range of 3 to 7.

According to an implementation of the present disclosure, there is provided a reconstituted formulation comprising (i) 5 to 35% (w/w) of the formulation comprising a) 0.05 to 10% (w/w) of Nebivolol or a pharmaceutically acceptable salt thereof, b) 0.4 to 10% (w/w) of a solubilizer; and c) 5 to 90% (w/w) of a sweetener; and (ii) 65 to 95% (w/w) of the liquid vehicle, wherein the reconstituted formulation is stable for a time period in the range of 30 days to one year.

According to an implementation of the present disclosure, there is provided a reconstituted formulation comprising the formulation a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; and i) 0.01 to 2% (w/w) of a coloring agent, with a liquid vehicle, wherein the reconstituted formulation is stable for a time period in the range of 30 days to one year, and the formulation has pH in the range of 3 to 7.

According to an implementation of the present disclosure, there is provided a process of preparing the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7, the process comprising: i) adding nebivolol or a pharmaceutically acceptable salt thereof with a solubilizer to obtain a first mixture; and ii) blending the first mixture with a sweetener to obtain the formulation.

According to an implementation of the present disclosure, there is provided a process of preparing the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7, the process comprising: i) adding nebivolol or a pharmaceutically acceptable salt thereof with a solubilizer to obtain a first mixture; and ii) blending the first mixture with a sweetener to obtain the formulation, wherein the formulation is blended with an excipient selected from a flavoring agent, a preservative, a binder, a buffer, a glidant, a coloring agent, or combinations thereof.

According to an implementation of the present disclosure, there is provided a process of preparing the formulation comprising: a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7, the process comprising: i) adding nebivolol or a pharmaceutically acceptable salt thereof with a solubilizer to obtain a first mixture; and ii) blending the first mixture with a sweetener to obtain the formulation, wherein the formulation is diluted with a liquid vehicle.

According to an implementation of the present disclosure, there is provided a process of preparing the formulation as disclosed herein, the process comprising: i) adding nebivolol or a pharmaceutically acceptable salt thereof with a solubilizer to obtain a first mixture; and ii) blending the first mixture with a sweetener and diluted with a liquid vehicle to obtain the formulation, followed by addition of an excipient selected from a flavoring agent, a preservative, a binder, a buffer, a glidant, a coloring agent, or combinations thereof; and wherein the formulation has pH in the range of 3 to 7.

According to an implementation of the present disclosure, there is provided a process of preparing the formulation as disclosed herein, the process comprising: i) adding nebivolol or a pharmaceutically acceptable salt thereof with a solubilizer to obtain a first mixture; and ii) the first mixture is diluted with a liquid vehicle comprising the sweetener to obtain the formulation; and wherein the formulation has pH in the range of 3 to 7.

According to an implementation of the present disclosure, there is provided a process of preparing the formulation as disclosed herein, the process comprising: i) adding nebivolol or a pharmaceutically acceptable salt thereof with a solubilizer to obtain a first mixture; and ii) the first mixture is diluted with the liquid vehicle comprising the sweetener, the flavoring agent, the preservative, the buffer, the coloring agent, or combinations thereof; and wherein the formulation has pH in the range of 3 to 7.

According to an implementation of the present disclosure, there is provided a process of preparing the formulation as disclosed herein, the process comprising: i) adding nebivolol or a pharmaceutically acceptable salt thereof with a solubilizer to obtain a first mixture; and ii) the first mixture is diluted with the liquid vehicle comprising the sweetener, the flavoring agent, the preservative, the buffer, the binder, the coloring agent, or combinations thereof, wherein the formulation has pH in the range of 3 to 7.

According to an implementation of the present disclosure, there is provided a process of preparing the formulation as disclosed herein, the process comprising: i) adding nebivolol or a pharmaceutically acceptable salt thereof with a solubilizer to obtain a first mixture; and ii) blending the first mixture with the sweetener, the flavoring agent, the preservative, the buffer, the binder, the coloring agent, or combinations thereof, wherein nebivolol or a pharmaceutically acceptable salt thereof is mixed with a liquid vehicle prior to adding with the solubilizer; and the formulation has pH in the range of 3 to 7.

According to an implementation of the present disclosure, there is provided a formulation as disclosed herein, wherein the formulation is administered orally.

According to an implementation of the present disclosure, there is provided a formulation as disclosed herein, wherein the formulation is a beta-blocker with β-adrenergic blocking ability.

According to an implementation of the present disclosure, there is provided a pharmaceutical composition comprising the formulation as disclosed herein with other pharmaceutically active compound.

According to an implementation of the present disclosure, there is provided use of the formulation as disclosed herein, as a beta-blocker and/or for abnormal blood pressures.

According to an implementation of the present disclosure, there is provided a kit comprising: i) the formulation comprising a) 0.05 to 10% (w/w) of Nebivolol or a pharmaceutically acceptable salt thereof; b) 0.4 to 10% (w/w) of a solubilizer; and c) 5 to 90% (w/w) of a sweetener, wherein the formulation has pH in the range of 3 to 7; and ii) a liquid vehicle.

According to an implementation of the present disclosure, there is provided a kit comprising: i) the formulation comprising a) 0.05 to 10% (w/w) of Nebivolol or a pharmaceutically acceptable salt thereof; b) 0.4 to 10% (w/w) of a solubilizer; c) 5 to 90% (w/w) of a sweetener; d) 0.05 to 20% (w/w) of a flavouring agent; e) 0.05 to 20% (w/w) of a preservative; f) 0.5 to 20% (w/w) of a binder; g) 0.025 to 15% (w/w) of a buffer; h) 0.1 to 3.0% (w/w) of a glidant; and i) 0.01 to 2% (w/w) of a coloring agent, wherein the formulation has pH in the range of 3 to 7; and ii) a liquid vehicle.

According to an implementation of the present disclosure, there is provided a kit comprising: i) the formulation comprising a) 0.1 to 50 mg/mL Nebivolol hydrochloride with b) 0.1 to 300 mg/ml of a solubilizer; and ii) a liquid vehicle comprising (a) 5 to 400 mg/ml of a sweetener; (b) 0.1 to 100 mg/ml buffer; (c) 0.5 to 50 mg/ml of a preservative; and (d) 0.5 to 20 mg/ml of a flavoring agent, wherein the liquid vehicle is water; and the pH of the formulation is in the range of 3 to 7.

According to an implementation of the present disclosure, there is provided an oral pharmaceutical dosage form comprising a dosing unit comprising the formulation as disclosed herein, wherein Nebivolol or a pharmaceutically acceptable salt thereof is in a final concentration equivalent to between 0.1 mg nebivolol HCl per ml liquid vehicle and 50 mg nebivolol HCl per ml liquid vehicle.

According to an implementation of the present disclosure, there is provided an oral pharmaceutical dosage form as disclosed herein, wherein the dosage form is single dosage form or multiple dosage form. In alternate implementation, there is provided an oral pharmaceutical dosage form as disclosed herein, wherein the dosage form is single dosage form. In another alternate implementation, there is provided an oral pharmaceutical dosage form as disclosed herein, wherein the dosage form is multiple dosage form, wherein the multiple dosage form is selected from two of the single oral dosage form, three of the single oral dosage form, four of the single oral dosage forms, or as per need thereof.

According to an implementation of the present disclosure, there is provided a method of administration in an individual in need thereof, the method comprising: administering a first amount of the formulation as disclosed herein, wherein the first amount of the formulation comprises Nebivolol or a pharmaceutically acceptable salt thereof in a final concentration equivalent to between 0.1 mg nebivolol HCl per ml liquid vehicle and 50 mg nebivolol HCl per ml liquid vehicle.

According to an implementation of the present disclosure, there is provided a method of administration in an individual in need thereof as disclosed herein, wherein the first amount of the formulation is in a single oral dosage form or multiple dosage form.

According to an implementation of the present disclosure, there is provided a method of administration in an individual in need thereof as disclosed herein, wherein the first amount is a single oral dosage form without a preservative, or a multiple oral dosage form with a preservative.

According to an implementation of the present disclosure, there is provided a method of treating or preventing a condition, disorder, or disease mediated by beta-blocking, the method comprising: administering an effective amount of the formulation as disclosed herein or the pharmaceutical composition, to a subject in need thereof.

According to an implementation of the present disclosure, there is provided a method of treating or preventing a condition, disorder, or disease mediated by beta-blocking, wherein the condition, disorder, or disease is selected from hypertension, or cardiovascular diseases.

According to an implementation of the present disclosure, there is provided formulation described herein are administered chronically. For example, in one implementations, a Nebivolol oral liquid formulation is administered as a continuous dose, i.e., administered daily to a subject. In other implementation, Nebivolol oral liquid formulations described herein are administered intermittently (e.g. drug holiday that includes a period of time in which the formulation is not administered or is administered in a reduced amount).

According to an implementation of the present disclosure, there is provided formulation described herein administered at a certain time of day for the entire administration period. For example, a Nebivolol oral liquid formulation can be administered at a certain time in the morning, in the evening, or prior to bed. In certain instances, a Nebivolol oral liquid formulation is administered in the morning. In other implementation, a Nebivolol oral liquid formulation can be administered at different times of the day for the entire administration period. For example, a Nebivolol oral liquid formulation can be administered on 8:00 am in the morning for the first day, 12 pm noon for the next day or administration, 4 pm in the afternoon for the third day or administration, and so on.

According to an implementation of the present disclosure, there is provided formulation described herein for treatment of certain diseases or conditions (e.g., hypertension, heart failure, myocardial infarction and the like) in a subject with a Nebivolol oral liquid formulation described herein encompass additional therapies and treatment regimens with other agents in some implementation. Such additional therapies and treatment regimens can include another therapy, e.g., additional anti-hypertensives, for treatment of the particular disease or condition in some implementation. Alternatively, in other implementation, additional therapies and treatment regimens include other agents used to treat adjunct conditions associated with the disease or condition or a side effect from the Nebivolol oral liquid formulation in the therapy.

According to an implementation of the present disclosure, there is provided formulation for use in combination with other pharmaceutically active compound which includes but not limited to diuretics such as loop, thiazide, potassium-sparing, and the like, beta blockers such as metoprolol, propanolol, pronethalol, and the like, alpha blockers such as phentolamine, phenoxybenzamine, tamsulosin, prazosin, and the like, mixed alpha and beta blockers such as bucindolol, carvedilol, labetalol, calcium channel blockers such as dihydropyridines such as nifedipine, amlodipine, etc., dilitazem, verapamil and the like, angiotensin II receptor antagonists such as saralasin, losartan, eprosartin, irbesartan, valsartan, and the like), other ACE inhibitors such as captopril, lisinopril, quinapril, ramipril, enalapril, zofenopril, and the like, aldosterone antagonists such as eplerenone, spironolactone and the like, vasodilators such as hydralazine and the like, or alpha-2 agonists such as clonidine, moxonidine, guanabenz and the like.

According to an implementation of the present disclosure, there is provided a formulation which is therapeutically active and bioequivalent to Bystolic® tablets.

Although the subject matter has been described in considerable detail with reference to certain examples and implementations thereof, other implementations are possible.

EXAMPLES

The disclosure will now be illustrated with the working examples, which is intended to illustrate the working of disclosure and not intended to take restrictively to imply any limitations on the scope of the present disclosure. Unless defined otherwise, all technical and scientific terms used herein have the same meaning as commonly understood to one ordinary person skilled in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The oral liquid formulations of the present invention are found to be therapeutically active and bioequivalent to Bystolic® tablets.

The following examples serve to provide further appreciation of the invention but are not meant in any way to restrict the effective scope of the invention.

EXAMPLES

Drug-Excipient Compatibility and Studies

Drug-Excipient compatibility study was carried with excipients such as mannitol, maltitol, dextrates, povidone, methyl paraben, propyl paraben, citric acid, sodium citrate, sodium saccharin. The study was carried out in clear glass vials with open air exposure at stress conditions 50° C. for 2 Weeks and 40° C./7.5% RH (relative humidity) for 1 month. The major impurity of Nebivolol i.e. desfluoro impurity was within the specification limits and Nebivolol was found to be stable.

Solubility of Nebivolol was evaluated in various solubility enhancers and data is presented Table 1 given below:

TABLE 1

| S. No | Excipient | Solubility of Nebivolol HCl (mg/ml) |
|---|---|---|
| 1 | Captisol (100 mg/ml) | 12.45 mg |
| 2 | Cyclodextrin (100 mg/ml) | 12.20 mg |
| 3 | Cyclodextrin (200 mg/ml) | 27.4 mg |
| 4 | Propylene Glycol | 8.3 mg |
| 6 | PEG 400 | 7.05 mg |
| 7 | PEG 4000 (100 mg/ml) | 2.08 mg |
| 8 | Labrasol | 2.40 mg |
| 9 | Tween 20 | 4.3 mg |
| 10 | Sodium lauryl sulfate (10 mg/mL) | 1 mg |
| 11 | Purified water | Insoluble |

Granules were prepared using propylene glycol and cyclodextrin mixture as granulating solvent and sorbitol powder, maltitol, dextrates, and sodium lauryl sulfate as powder blend to adsorb Nebivolol. The wet granules were dried in oven at 50° C. and resultant granules were reconstituted with water to yield 1 mg/mL of Nebivolol solution. It was observed that the granules obtained using cyclodextrin as the solubilizer, although showed the high solubility initially, however, when reconstituted, due to its high solubility character, the active compound, i.e., nebivolol got precipitated. Thus, the selection of solubilizer was optimized.

Similarly, the use of sweetener in the formulation was optimized. Sweetener, such as lactose form Maillard adduct and hence not suitable for use in the formulation. And acesulfame is not compatible with sodium lauryl sulfate.

Alternatively, sorbitol powder or mixture of sorbitol powder and sodium lauryl sulfate was granulated initially using propylene glycol and Nebivolol (7 mg/ml) as granulating solvent. Various combination of these formulations were prepared and tested for stability as given in Table 2 below.

TABLE 2

| S.No. | Ingredient | Granulating solvent |
|---|---|---|
| 1 | Sorbitol Powder | propylene glycol and Nebivolol (7 mg/ml) |
| 2 | Sorbitol Powder + SLS (100 mg) | propylene glycol and Nebivolol (7 mg/ml) |
| 3 | Sorbitol Powder + SLS (200 mg) | propylene glycol and Nebivolol (7 mg/ml) |
| 4 | Sorbitol Powder | propylene glycol and Nebivolol (10 mg/ml) |
| 5 | Sorbitol Powder + SLS (100 mg) | propylene glycol and Nebivolol (10 mg/ml) |
| 6 | Sorbitol Powder + SLS (200 mg) | propylene glycol and Nebivolol (10 mg/ml) |
| 7 | Dextrates + SLS | propylene glycol and (12 mg/ml) |

After reconstitution, stability of the solution was tested and desfloro impurity was within the specification limits and the solution was found to be stable after 24 hrs at RT.

Stability at Different pH Condition

To evaluate the stability of Nebivolol in suitable liquid vehicle or solubilizer at different pH conditions, pH stability study was performed using 0.1N HCL/0.1N NaOH for pH adjustment. Propylene glycol was used as solubilizer to dissolve Nebivolol to prepare the stock solution. The stock solution was added to water and adjusted the pH with 0.1N HCL/0.1N NaOH at different pH ranging from 3 to 7.

The solution of Nebivolol in propylene glycol was tested for desfluoro Nebivolol impurity and found to be within the specification limits when tested 50° C. for 1M and 40° C./75% RH for 6M accelerated conditions and Nebivolol was found to be stable.

Examples 1-4

Nebivolol Powder for Oral Solution

Table 3 provides the powder formulation of Nebivolol with other components along with their weight percentages. The powder formulation can be reconstituted in a liquid vehicle for administration as oral solution.

TABLE 3

| Ingredients | 1 | 2 | 3 | 4 |
|---|---|---|---|---|
| | % w/w | | | |
| Nebivolol HCl | 0.87 | 0.88 | 0.87 | 0.88 |
| Sodium Lauryl Sulphate | 8.77 | 8.84 | 8.77 | 8.84 |
| Sorbitol Powder | 87.71 | 88.49 | 87.71 | 88.49 |
| Sucralose | 0.87 | 0.88 | 0.87 | 0.88 |

TABLE 3-continued

| Ingredients | 1 | 2 | 3 | 4 |
|---|---|---|---|---|
| | % w/w | | | |
| Sodium Benzoate | 0.87 | — | — | — |
| Methyl Paraben Sodium | — | — | 0.87 | — |
| Strawberry Flavour | 0.87 | 0.88 | 0.87 | — |
| Orange Flavour | — | — | — | 0.88 |
| Total | 100 | 100 | 100 | 100 |

Preparation Process of the Formulation:

A solution of Nebivolol and sodium lauryl sulphate was prepared. Sorbitol powder and sucralose was blended and to this, a solution of Nebivolol and sodium lauryl sulphate was sprayed to obtain granules. The wet granules were dried and blended with sodium benzoate, methyl paraben sodium and strawberry flavour to obtain Nebivolol powder for solution. The power/granules obtained were blended with silicon dioxide and filled into sachets and bottles.

Alternatively, the powder for solution was also prepared using spray dried method as described below:

A solution of Nebivolol and sodium lauryl sulphate was prepared and spray dried. To this, a mixture of sorbitol powder and sucralose was added, followed by sodium benzoate, methyl paraben sodium and strawberry flavour and blended to obtain Nebivolol powder for solution.

The compositions described herein are filled into Sachets (for single use) and HDPE bottles, each bottle contains 4.56 g of powder for solution. Each bottle was reconstituted with 36 ml of purified water to provide an oral solution formulation with specified concentration of Nebivolol. For Example, 0.88% (w/w) of powder upon reconstitution yields 1 mg/mL solution.

Reconstitution Process of Powder for Oral Solution from HDPE Bottle

The reconstitution process include the following steps: 1. Shaken one bottle of powder for oral Solution (4.56 g) to loosen the powder, opened the bottle and then removed the induction seal liner. 2. added approximately 36 mL of the water/liquid vehicle using a graduated cylinder or a syringe measure to the powder. Tightly closed the HDPE bottle and shook vigorously by hand continuously for 3 minutes. 3. Allowed the bottle to sit for about 1 minute. 4. After reconstitution, 40 mg of Nebivolol HCl is contained in 40 mL of the solution. Swirled (gently shook) before dispensing a dose.

Stability Testing of Powder for Oral Solution (POS)

The Powder for Oral Solution/suspension formulations described in Example 5 to 8 (Table 3) were stored at 40° C./75% RH and at 50° C. in open exposure containers for 1M. After storage, the samples were evaluated for assay, impurities, appearance, and odor. The POS formulations and corresponding solution formulations described herein are found to be stable with minimum impurities and is compatible with the pharmaceutical standards. Stability data of these formulations is given in Table 4 below:

TABLE 4

| | Test parameters | | | |
|---|---|---|---|---|
| | 1 | | 2 | |
| | 50° C. 1M | 40° C./75 RH 1M | 50° C. 1M | 40° C./75 RH 1M |
| Assay | 99 | 100 | 105 | 100 |
| Related substances | | | | |
| Desfloro imp | 0.11 | 0.03 | 0.07 | 0.03 |
| Unknown imp | 0.18 | 0.19 | 0.22 | 0.14 |
| Total imp | 0.29 | 0.22 | 0.29 | 0.17 |
| | Test parameters | | | |
| | 3 | | 4 | |
| | 50° C. 1M | 40° C./75 RH 1M | 50° C. 1M | 40° C./75 RH 1M |
| Assay | 99 | 94 | 91 | 99 |
| Related substances | | | | |
| Desfloro imp | 0.25 | 0.08 | 0.05 | 0.05 |
| Unknown imp | 0.32 | 0.25 | 0.17 | 0.14 |
| Total imp | 0.57 | 0.33 | 0.22 | 0.19 |

Example 5

Nebivolol Powder for Oral Solution

TABLE 5

| S. No | Ingredient | Qty/ml |
|---|---|---|
| 1 | Nebivolol HC1 | 1 mg |
| 2 | Sodium Lauryl Sulphate | 10 mg |
| 3 | Sorbitol Powder | 100 mg |
| 4 | Sodium Saccharin | 2 mg |
| 5 | Orange Flavour | 2 mg |
| 6 | PVP K-90 | 10 mg |

The powder formulation described above in Table 5 was prepared using the process similar to the one disclosed above for Example 1 (Table 3).

Example 6

Nebivolol Powder for Oral Solution

TABLE 6

| Ingredients | % w/w |
|---|---|
| Nebivolol HCl | 0.88 |
| Sodium Lauryl Sulphate | 8.8 |
| Xylitol | 88.5 |
| Sucralose | 0.94 |
| Strawberry Flavour | 0.88 |
| Total | 100 |

Example 7

Nebivolol Powder for Oral Solution

TABLE 7

| Ingredients | % w/w |
|---|---|
| Nebivolol HCl | 0.88 |
| Sodium Lauryl Sulphate | 5.6 |
| PEG 400 | 3.2 |
| Xylitol | 88.5 |
| Sucralose | 0.94 |
| Strawberry Flavour | 0.88 |
| Total | 100 |

The powder formulation described above in Tables 6 and 7 were prepared using the process similar to the one disclosed above for example 1 (Table 3).

Example 8-10

Nebivolol Hydrochloride Powder Reconstituted with Liquid Vehicle

Nebivolol HCl (5 mg) powder was blended with sodium lauryl sulphate (10 mg). The blend was filled in an HDPE bottle and reconstituted with liquid vehicle comprising the below ingredients. In Table 8, given below is the composition of liquid vehicle used to reconstitute the powdered blend:

TABLE 8

| Components | 8 | 9 | 10 |
|---|---|---|---|
| Artificial Grape Flavor | 50 mg | 75 mg | 100 mg |
| Citric Acid (anhydrous) | 25 mg | 35 mg | 50 mg |
| Sucralose | 10 mg | — | — |
| Xylitol | — | 200 mg | 300 mg |
| Saccharin sodium | — | — | — |
| D&C Yellow No. 10, FD&C Red No. 40 | 1 mg | 0.5 mg | 2 mg |
| Sodium Benzoate | 10 mg | — | 20 mg |
| Methyl paraben | — | 10 mg | — |
| Propylparaben | — | 1 mg | — |
| Purified water QS to | 1 mL | 1 mL | 1 mL |

Example 11—Nebivolol Oral Liquid

TABLE 9

| S. No | Ingredient | Qty/ml |
|---|---|---|
| 1 | Nebivolol HCl | 1 mg |
| 2 | Sodium Lauryl Sulphate | 10 mg |
| 3 | Sorbitol Powder | 100 mg |
| 4 | Sucralose | 4 mg |
| 5 | Orange Flavour | 2 mg |
| 6 | PVP K-90 | 10 mg |
| 7 | Purified water | Qs to 1 ml |

Example 11 of Table 9 was prepared by the process described herein. Sodium lauryl sulphate was added to water, followed by Nebivolol, Sorbitol Powder, Sucralose, Orange Flavour, PVP K-90 and uniformly mixed to obtain solution.

The formulation yielded clear solution and was subjected to stress testing at 50° C. for 2 W and under accelerated stability condition at 40° C./75% RH for 2M. 30 cc HDPE bottles were used as container closure system. The data is presented in Table 10 below.

TABLE 10

| Test Parameters | | | |
|---|---|---|---|
| Condition | Initial | 50° C. 2W | 40° C./75% RH 2M |
| Assay | 100.5 | 96.5 | 99.5 |
| pH | 6.56 | 6.34 | 6.41 |
| Related substances | | | |
| Desfloro imp | 0.01 | 0.03 | 0.03 |
| Related comp-A | 0.01 | ND | ND |
| Unknown Imp | ND | 0.04 | 0.16 |
| Total imp | 0.02 | 0.07 | 0.19 |

The formulation was to be stable in stress as well as accelerated conditions. The formulation was found to have the least impurities and is compatible with the pharmaceutical standards.

The liquid formulations described in examples given below were prepared using the process similar to the one disclosed above for example 10.

Example 12 Nebivolol Oral Liquid

TABLE 11

| S. No | Ingredient | Qty (mg)/ml |
|---|---|---|
| 1 | Nebivolol HCl | 0.87 |
| 2 | PEG 4000 | 7.8 |
| 3 | Maltitol | 89.8 |
| 4 | sodium benzoate | 0.75 |
| 5 | Strawberry Flavour | 0.8 |
| 6 | Purified water | Qs to 1 ml |

Example 13—Nebivolol Oral Liquid

TABLE 12

| S. No | Ingredient | Qty (mg)/ml |
|---|---|---|
| 1 | Nebivolol HCl | 0.87 |
| 2 | Poloxamer 188 | 5.1 |
| 3 | Maltitol | 92.5 |
| 4 | sodium benzoate | 0.75 |
| 5 | Strawberry Flavour | 0.8 |
| 6 | Purified water | Qs to 1 ml |

Example 14—Nebivolol Oral Liquid

TABLE 13

| S. No | Ingredient | Qty (mg)/ml |
|---|---|---|
| 1 | Nebivolol HCl | 0.87 |
| 2 | Sodium lauryl sulfate | 8.7 |
| 3 | Maltitol | 89.2 |
| 4 | sodium benzoate | 0.75 |
| 5 | Strawberry Flavour | 0.7 |
| 6 | Purified water | Qs to 1 ml |

Example 15—Nebivolol Oral Liquid

TABLE 14

| S. No | Ingredient | Qty (mg)/ml |
|---|---|---|
| 1 | Nebivolol HCl | 0.87 |
| 2 | PEG 4000 | 9.3 |
| 3 | Xylitol | 88.1 |
| 4 | sodium benzoate | 0.91 |
| 5 | Strawberry Flavour | 0.91 |
| 6 | Purified water | Qs to 1 ml |

Example 16—Nebivolol Oral Liquid

TABLE 15

| S. No | Ingredient | Qty (mg)/ml |
|---|---|---|
| 1 | Nebivolol HCl | 0.87 |
| 2 | PEG 4000 | 9.4 |
| 3 | Sorbitol | 88.1 |
| 4 | sodium benzoate | 0.85 |
| 5 | Strawberry Flavour | 0.85 |
| 6 | Purified water | Qs to 1 ml |

Example 17—Nebivolol Oral Liquid

TABLE 16

| S. No | Ingredient | Qty (mg)/ml |
|---|---|---|
| 1 | Nebivolol HCl | 1 |
| 2 | Sodium Lauryl Sulphate | 10 |
| 3 | Sorbitol Powder | 100 |
| 4 | Sodium Saccharin | 2 |
| 5 | Orange Flavour | 2 |
| 6 | PVP K-90 | 10 |
| 7 | Purified water | Qs to 1 ml |

The formulations yielded clear solution, and was subjected to stress testing at 50° C. for 2 W and under accelerated stability condition at 40° C./75% RH for 2M with no or minimum impurities. 30 cc HDPE bottles were used as container closure system. The data is presented Table 17 below.

TABLE 17

| Test Parameters | | | |
|---|---|---|---|
| Condition | Initial | 50° C. 2W | 40° C./75% RH 2M |
| Assay | 101.2 | 98.9 | 100.5 |
| pH | 6.76 | 6.49 | 6.53 |
| Related substances | | | |
| Desfloro imp | 0.03 | 0.04 | ND |
| Related comp-A | ND | ND | ND |
| Unknown Imp | ND | 0.06 | 0.11 |
| Total imp | 0.03 | 0.10 | 0.11 |

The formulation was found to be chemically stable in stress as well as accelerated conditions.

Example 18—Nebivolol Oral Liquid

TABLE 18

| S. No | Ingredient | Qty (mg)/ml |
|---|---|---|
| 1 | Nebivolol HCl | 1 |
| 2 | Sodium Lauryl Sulphate | 10 |
| 3 | Sorbitol Solution 70/02B | 200 |
| 4 | Strawberry Flavour | 2 |
| 5 | Purified water | Qs to 1 ml |

The formulation trial was subjected to stress testing at 50° C. for 2 W and accelerated stability condition at 40° C./75% RH for 2M. The data is presented in Table 19 below.

TABLE 19

| Test Parameters | | | |
|---|---|---|---|
| Condition | Initial | 50° C. 2W | 40° C./75% RH 2M |
| Assay | 100.9 | 99.9 | 100.3 |
| pH | 7.01 | 6.03 | 6.43 |
| Related substances | | | |
| Desfloro imp | 0.03 | 0.05 | 0.04 |
| Related comp-A | ND | ND | ND |
| Unknown Imp | ND | ND | 0.19 |
| Total imp | 0.03 | 0.05 | 0.23 |

The Formulation was found to be chemically stable in stress as well as accelerated conditions with least or no impurities.

Example 19—Nebivolol Oral Liquid

TABLE 20

| S. No | Ingredients | Qty/ml |
|---|---|---|
| 1 | Nebivolol HCl | 1 mg |
| 2 | Sodium Lauryl Sulphate | 10 mg |
| 3 | Citric acid anhydrous | 0.4 mg |
| 4 | Sodium benzoate | 1 mg |
| 6 | Sorbitol Powder | 100 mg |
| 7 | Sucralose | 2 mg |
| 8 | Strawberry Flavour | 2 mg |
| 9 | Purified water | Qs to 1 ml |

The formulation trial yielded stable solution with a physical observation of clear colourless solution and it is evaluated for accelerated stability condition at 40° C./75% RH. The data is presented in Table 21 below.

TABLE 21

| Test Parameters | | | |
|---|---|---|---|
| | | 40° C./75% RH | |
| Condition | Initial | 1M | 2M |
| Assay | 101.7 | 100.8 | 101.7 |
| pH | 4.55 | 4.52 | 4.54 |
| Related substances | | | |
| Desfloro imp | 0.04 | 0.02 | 0.04 |
| Related comp-A | ND | ND | ND |

TABLE 21-continued

| Test Parameters | | | |
|---|---|---|---|
| | | 40° C./75% RH | |
| Condition | Initial | 1M | 2M |
| Unknown Imp | ND | ND | 0.02 |
| Total imp | 0.04 | 0.02 | 0.06 |

The above data shows the formulation is chemically stable under accelerated conditions for 2 months with no impurities and met the pharmaceutical standards.

Although examples for the present disclosure have been described in language specific to structural features and/or methods, it is to be understood that the appended claims are not limited to the specific features or methods described herein. Rather, the specific features and methods are disclosed and explained as exemplary implementations of the present disclosure.

Advantages of the Present Disclosure

The present disclosure provides a stable oral formulation comprising 0.05 to 10% (w/w) of Nebivolol or a pharmaceutically acceptable salt thereof, 0.4 to 10% (w/w) of a solubilizer; and 5 to 90% (w/w) of a sweetener, wherein the formulation has pH in the range of 3 to 7. The present disclosure provides oral formulation in powder form which can be reconstituted with a suitable liquid vehicle. The formulation of the present disclosure are available for reconstitution with varied liquid vehicle selected from water, ethyl alcohol, glycerin, syrup, juices, beverages, or combinations thereof. The formulation of the present disclosure is stable and suitable for oral administration. The liquid formulation is stable for longer periods in the range of 30 days to 12 months. The formulation can be administered as a single dosage or as multiple dosage. The formulations of the present disclosure has improved taste and is suitable for pediatric and geriatric population and for those who have difficulty in swallowing tablets or capsules. The liquid formulation of the present disclosure has increased solubility and stability, thereby improving their bioavailability and thereby the pharmaceutical activity of Nebivolol. The formulation of the present disclosure is a beta-blocker with β-adrenergic blocking ability. The formulation of the present disclosure is a beta-blocker with β-adrenergic blocking ability for use as a beta-blocker and/or for treating abnormal blood pressures. The formulation of the present disclosure may also be used in combination with other pharmaceutical active compound selected from diuretics, beta blockers, alpha blockers, mixed alpha and beta blockers, calcium channel blockers, angiotensin II receptor antagonists, ACE inhibitors, aldosterone antagonists, or alpha-2 agonists. The present disclosure also provides a method of administration of the formulation to a subject in need thereof either in single dosage or in multiple dosage. The formulation is stable for use as multiple dosage form. The present disclosure also provides a method for treating or preventing a condition, disorder, or disease mediated by beta-blocking selected from hypertension, or cardiovascular diseases.

We claim:

1. An oral liquid formulation comprising:
   a. 0.1 to 2% (w/w) of nebivolol hydrochloride as the sole active ingredient;
   b. 5 to 10% (w/w) of a solubilizer selected from the group consisting of cyclodextrin, propylene glycol, polyethylene glycol, polysorbate 20, polysorbate 80, sorbitan monooleate, poloxamer, sodium lauryl sulfate and mixtures thereof;
   c. 70 to 90% (w/w) of one or more sweeteners selected from the group consisting of glucose, fructose, sucrose, xylitol, tagatose, sucralose, maltitol, isomaltulose, lactitol, sorbitol, erythritol, trehalose, maltodextrin, polydextrose, inulin, acesulfame, alitame, aspartame, neotame, sodium cyclamate, saccharin and mixtures thereof;
   d. 0.5 to 1% (w/w) of a preservative selected from the group consisting of ascorbic acid, benzyl alcohol, butylated hydroxyanisole, butylated hydroxytoluene, sodium benzoate, sodium bisulfate, sodium metabisulfite, sodium sulfite, methyl paraben, propylparaben, benzoic acid, potassium sorbate, and mixtures thereof; and
   e. a liquid vehicle selected from the group consisting of water, ethyl alcohol, syrup and mixtures thereof;

wherein the formulation has a pH in the range of from 3 to 7 and the formulation has less than 1% (w/w) of each of the desfluoro nebivolol and 4-benzylated nebivolol impurities, when stored at a temperature of about 25±5° C. for a time period in the range of from 30 days to one year.

2. The oral liquid formulation of claim 1, wherein the formulation comprises from 0.1 to 50 ml of the vehicle.

3. The oral liquid formulation of claim 1, further comprising from 0.1 to 1% (w/w) of a flavouring agent.

4. The oral liquid formulation of claim 3, wherein the flavouring agent is selected from the group consisting of strawberry, cherry, grape, orange, peppermint, vanilla, bubble gum, and mixtures thereof.

5. The oral liquid formulation of claim 1, further comprising from 0.025 to 5% of a buffer.

6. The oral liquid formulation of claim 5, wherein the buffer is selected from the group consisting of citric acid, sodium citrate, sodium tartarate, sodium acetate, sodium carbonate, sodium polyphosphate, potassium polyphosphate, sodium pyrophosphate, potassium pyrophosphate, disodium hydrogenphosphate, trisodium phosphate, sodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, and calcium bicarbonate.

7. The oral liquid formulation of claim 1, wherein the formulation has less than 5% (w/w) of total impurities, when stored at about 25±5° C. for a time period in the range of from 30 days to one year.

* * * * *